United States Patent [19]

Tany

[11] 4,055,190

[45] Oct. 25, 1977

[54] ELECTRICAL THERAPEUTIC APPARATUS

[76] Inventor: Michio Tany, No. 2-24-12, Minami Aoyama, Minato, Tokyo, Japan

[21] Appl. No.: 534,430

[22] Filed: Dec. 19, 1974

[51] Int. Cl.$^2$ .............................................. A61N 1/36
[52] U.S. Cl. .............................. 128/422; 128/2.1 C; 128/303.18; 128/329 A
[58] Field of Search .................. 128/419 R, 420, 421, 128/422, 423, 2.1 C, 2.1 R, 303.17, 303.18, 329 A

[56] References Cited

U.S. PATENT DOCUMENTS

| 2,350,797 | 6/1944 | Morland et al. | 128/421 |
| 2,375,575 | 5/1945 | Morland et al. | 128/421 |
| 2,532,788 | 12/1950 | Sarnoff | 128/421 |
| 2,838,672 | 6/1958 | Paust | 128/422 |
| 3,056,409 | 10/1962 | Edwards | 128/422 |
| 3,207,151 | 9/1965 | Takagi | 128/2.1 R |
| 3,245,408 | 4/1966 | Gonser | 128/422 |
| 3,411,507 | 11/1968 | Wingrove | 128/422 |

FOREIGN PATENT DOCUMENTS

| 997,670 | 7/1965 | United Kingdom | 128/2.1 R |

Primary Examiner—William E. Kamm

[57] ABSTRACT

An electrical therapeutic apparatus which comprises an oscillator for selectively generating a low or high frequency, a selector associated with said oscillator to determine a voltage having an intrinsic frequency of specified wave suitable to an affected meridian and a means for applying the selected voltage to the human body. The voltage at the selected frequency of specified wave is applied to a reaction point communicated through meridian with entrails in the body.

5 Claims, 15 Drawing Figures

FIG.6

FIG. 13
Pain Threshold Changes
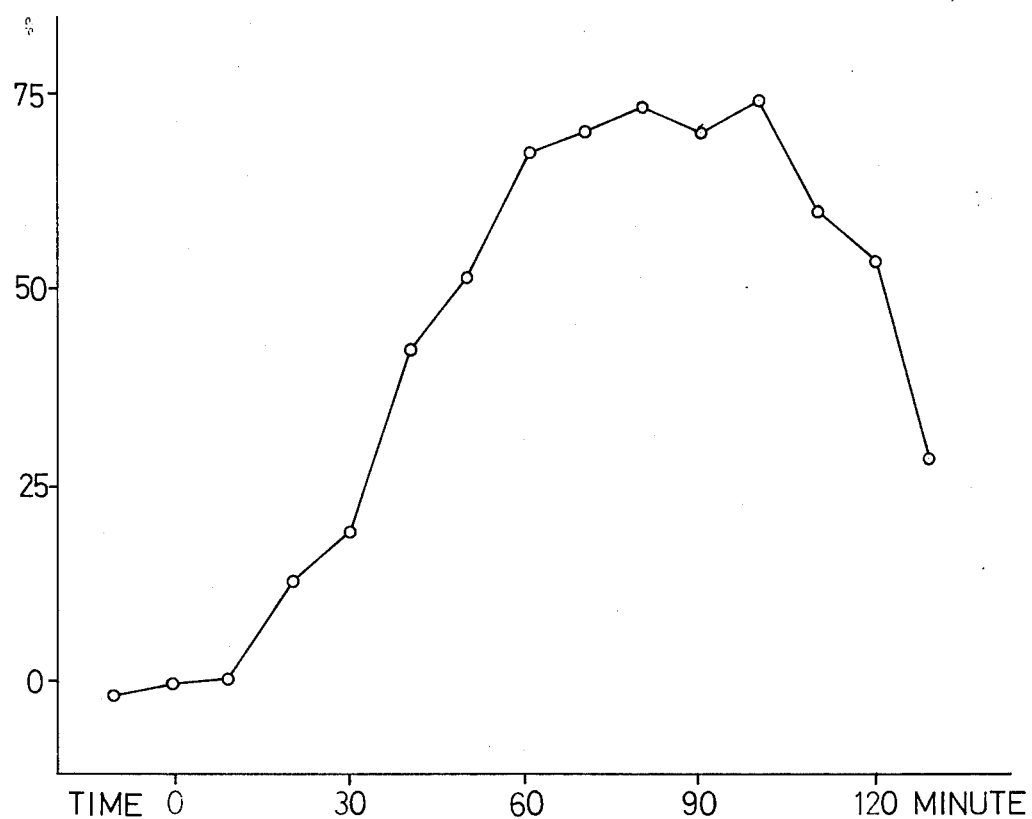
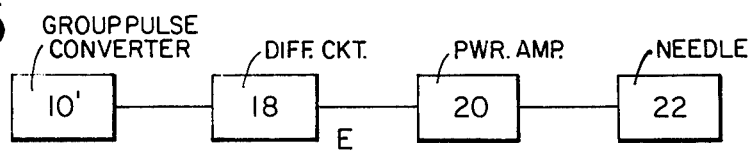
FIG. 15

4,055,190

ELECTRICAL THERAPEUTIC APPARATUS

BACKGROUND AND SUMMARY OF THE INVENTION

This invention relates to an improvement in the conventional acupuncture therapy and more particularly to an electrical therapeutic apparatus for curing various diseases and bodily disorders by applying a voltage at a selected frequency and wave shape including a low frequency and a high frequency to a diagnostic point on the affected meridians in the human body.

Acupuncture, one aspect of Oriental medicine, dates almost as far back as Oriental history itself. It was first described in detail as early as the 4th Century B.C. in the ancient Chinese documents on medicine and constituted the main major branch of medicine in the Orient until more recent times when Western medicine gained popularity.

Acupuncture is based on the theory that the physiological activity of the body is controlled by 12 meridians which flow through the body which, in turn is governed by the universe, the natural phenomena surrounding the individual and his psychological disposition. The origin and cause of various diseases and bodily disorders are defined as an abnormality or imbalance in the flow of energy through these meridians. This imbalance can be corrected using a highly sophisticated technique which involves the stimulation of various points along the meridian. This technique also produces an exceedingly effective relief for pain which has been realized and put into practical use for a period of approximately 3,000 years. The strength and duration of this pain killing effect is sufficiently powerful to endure even a surgical procedure, however, not until recently has it been used in surgery. In most cases, the acupuncture therapy is carried out depending upon the therapeutist's highly sophisticated technique.

Recently there has been proposed and practiced an electric acupuncture therapy where a specific voltage is applied to the human body through needles to obtain anesthetic and analgetic effects in various reaction points on the affected meridian in the body. However, the conventional electric acupuncture therapy is not normally endorsed by scientific and clinical experiments but merely used as an electrical stimulator with insufficient therapeutical effects.

In view of these backgrounds, my research has been directed to replace an ancient Chinese medicine by a sophisticated electrical therapy by simply selecting and regulating the voltage to be applied to the human body.

After an extensive research, I have found out that various kinds of diseases may be cured by applying a predetermined voltage of selected frequency of specific wave shape suitable to the affected meridian corresponding to the deficient or excessive point in the body to balance with the meridian on the healthy point and that the specific frequency may be preferably selected from the range between 2.5 KHz to 1.6 MHz in accordance with the condition of the patient.

Further, the acupuncture therapy is usually used with a view to obtaining two therapeutical effects in accordance with two different therapeutic methods referred to as "tonification" and "sedation." The electrical therapeutic apparatus, therefore, should have a capability of attaining at least two different therapies.

The tonification and sedation used in the acupuncture therapy have counter functions. The tonification increases the deficient reaction at selected acupuncture points with a soft and mild stimulation for a relatively extended period.

On the other hand, sedation decreases and any excessive reaction at the selected acupunture point to a strong and destructive stimulation over a short period.

A general object of my inventions, therefore, is to provide a new electrical therapeutic apparatus for applying a predetermined voltage having a frequency of the specific wave to the human body.

BRIEF DESCRIPTION OF THE DRAWINGS

FIG. 6 is a diagram of the group pulse wherein the pulse amplitude is progressively increased to moderate the stimulation;

FIG. 13 is a graphical diagram showing the pain threshold changes during the acupuncture anesthesia;

FIG. 15 is a block circuit diagram showing group pulse waves obtainable in accordance with the present invention.

DETAILED DESCRIPTION OF THE PREFERRED EMBODIMENT

Figure 1:
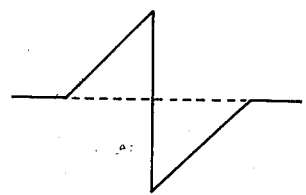
FIG. 1 is a diagram of the pulse wave adapted to be predominantly used for the tonification.
Figure 2:
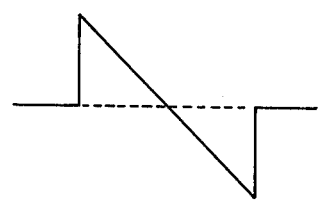
FIG. 2 is a diagram of the pulse wave adapted to be predominantly used for the sedation.

In accordance with my invention, the foregoing two different stimulations may be electrically accomplished by voltages of different frequencies having relatively a slow rise pulse in the shape as shown in FIGS. 1 and 2 effective to the tonification and sedation respectively.

Figure 3:
FIG. 3 is a diagram of continuous series and an intermittent series of pulses at predetermined frequencies useful for the tonification procedure.

Further, I discovered that continuous low frequency pulses (FIG. 3, line a for example) or an intermittant low frequency pulse (FIG. 3, line b) are preferred to the tonification for a weak stimulation.

Figure 4:
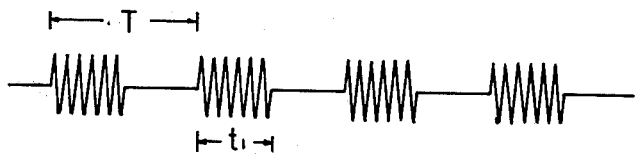
FIG. 4 is a showing of an intermittent series of pulses at predetermined frequency and intervals useful for sedation.

On the other hand, the intermittent frequencies at more than 0.05KHz as shown in FIG. 4 is preferred to the sedation for a strong stimulation.

In accordance with my invention, the electrical therapeutic apparatus comprises an oscillator for selectively generating a low or high frequency, a selector associated with said oscillator to select a voltage having the frequency and wave shape suitable to an affected meridian and a means for applying the selected voltage to the human body.

The oscillator contains a known oscillation circuit which is capable of selectively generating a relatively low voltage at frequencies between 2.5 KHz to 1.6 MHz. A switch system may be used for selecting the frequency of the oscillation and wave shape and the frequency selected will depend on the ailment to be treated and accordingly the affected meridian. The switch system and oscillator in which the switch system is incorporated are conventional components. The switch system is advantageously designed to select those frequencies which have been found to ameliorate the discomfort to be treated by the apparatus of the invention. Thus, for example, as will be seen from the ensuing disclosure, when the affected meridian is the large intestine meridian, the switch will select a frequency of 160 KHz. The switch system varies the frequency of the oscillator by suitably selecting the R-C constant to the oscillator. This may be done by a rotatable switch arm adapted to engage different voltage divider networks constituted of resistors connected in series with capacitors, each resistor and capacitor network determining a time constant of the oscillator circuit, as is well known in the art.

The selected voltage at predetermined frequency is applied to two different reaction points on the meridian in communication with the diagnostic point in the human body for a predetermined time period to cure the disease point with anesthetic and analgestic effects without entailing any harmful effects. The operating time of the oscillator may be controlled by a timer.

As hereinbefore described, the frequency effective to obtain remarkable therapeutic effects presents in the range between 2.5 KHz-1.6 MHz from which the most suitable frequency by a given meridian is selected to achieve the intended therapy. From my clinical experiments, it has been confirmed that the frequency at 10 KHz is very effective when applied to the stomach meridian for example between the Hoku point (ST 12 or 2) and the Tsusanri point (ST 36) whereas the frequency at 100 KHz is very effective when applied to the liver meridian for example between the Taisho point (L 3) and the Shomon point (LI 13).

Also as hereinbefore described, the voltage of selected frequency is applied to the human body through an electrode such as a needle and the like.

In the conventional electrical acupuncture therapy, a voltage of single polarity in either positive or negative and more particularly positive component is applied to the body through the needle which often causes an electrolytic reaction with corrosion or melting of needle and undesired reaction in the skin.

To avoid the foregoing disadvantages, the electrical therapeutic apparatus as another embodiment of my invention is comprised of an oscillator for generating a pulse frequency in conformity with an intrinsic oscillation cycle ($\frac{1}{2}$-10 seconds) of the human body, a converter being provided for convertint the pulse into a single oscillation pulse having a duration of less than 1/5,000 seconds in which the difference between the positive and negative components of the pulse is diminished or erased, and a means is provided for applying a pulse signal to the human body. Generally, the positive or negative component of a pulse causes an undesirable electrolytic reaction at an acupuncture point which is energized by the pulse. However, when the positive and negative components of the pulse are equal in absolute value but opposite in sign, the reaction by the positive component of a cycle is erased by that by the negative component of the cycle so that no undesirable reaction remains in a single cycle.

In accordance with this embodiment a single pulse which oscillates at a cycle equivalent to an intrinsic oscillation cycle of the human body in positive and negative directions in every cycle is supplied to the human body through the acupuncture needle so that the neutralized voltage is applied to the body without causing any undesired electrolytic reaction. "An intrinsic oscillation of the human body" is an oscillation which is produced and observed in the respective human body and characteristic to the human body. This oscillation varies with human bodies, meridians and affections and affections or diseases. The apparatus according to the present invention supplies pulses which oscillate at a cycle equivalent to the intrinsic oscillation of the human body but the cycle is selected by the operator or the doctor.

Figure 5:
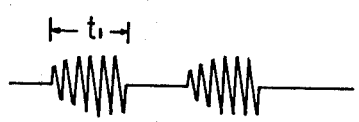
FIG. 5 is a diagram of group pulses, hereinafter referred to as group pulses effective to stimulate the affected part of the body.

When a constant pulse at a constant frequency is applied to the body for an extended period, the body cell tissue against the stimulation reaction becomes chronic with considerable lowering of the anesthetic and analgetic effects. To avoid this undesired phenomenon, it is preferred to vary the pulse duration. For this purpose, a group pulse having a duration $t_1$ of less than 5 seconds and an oscillation cycle of less than 1/50 seconds is intermittently generated in the body which has an intrinsic oscillation cycle of $\frac{1}{2}$-10 seconds as illustrated in FIG. 5. In this case to avoid an excessive stimulation by an initial rising of the group pulse it is advantageous to gradually increase the pulse amplitude as shown in FIG. 6.

It is, therefore, another aspect of the invention to provide an electrical acupuncture therapeutic apparatus which comprises an oscillator for generating a pulse of specific frequency in conformity with an intrinsic oscillation cycle ($\frac{1}{2}$-10 seconds) of the human body, a converter for generating a group of pulses in every oscillation cycle of the pulse, said group of pulses having an oscillation cycle of less than 1/50 seconds and a duration of less than 5 seconds in which a difference between positive and negative components is diminisheed or erased, a means being provided for applying a resulting signal to the body.

Figure 7:
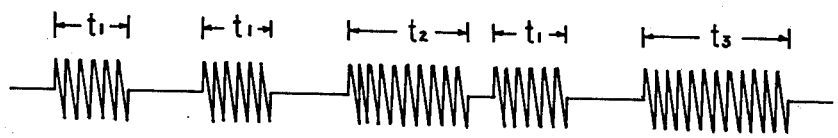
FIG. 7 is a showing of the group pulses having different time durations.
Figure 8:
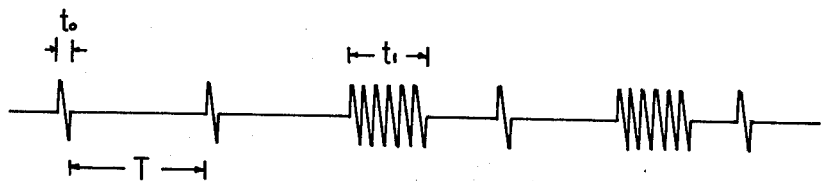
FIG. 8 is a diagram of single pulses interspersed with group pulses showing anesthetic and analgesic effects.

Moreover, in order to enhance the anesthetic and analgesic effects, it is preferred to add a pulse group, e.g., $t2$ or $t3$ of larger duration than that of the shorter pulse $t1$ group duration as shown in FIG. 7. It is also advantageous to intersperse single pulses $t$ to with group pulses in periodic or aperiodic fashion as shown in FIG. 8.

Figure 9:
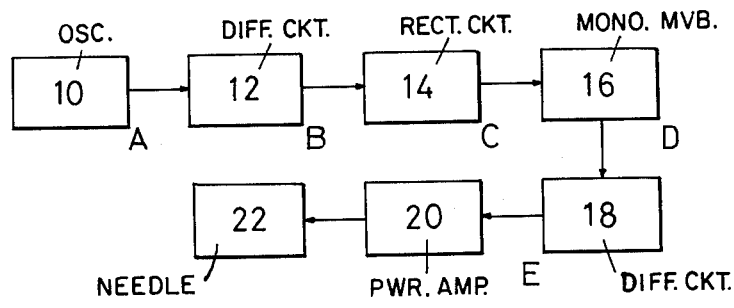
FIG. 9 is a block circuit diagram of the electrical therapeutical apparatus in accordance with the invention.
Figure 10:
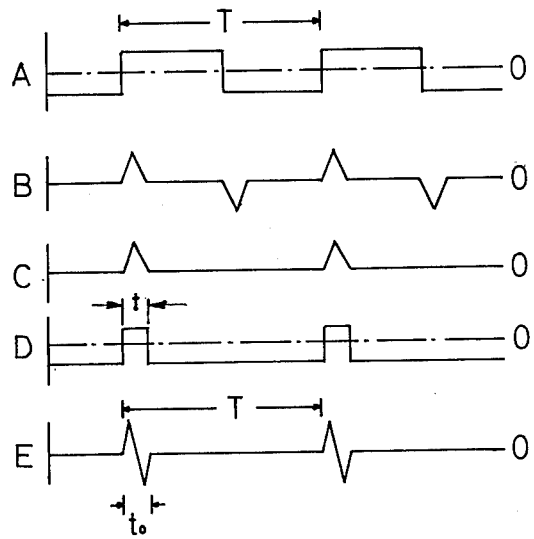
FIG. 10 is a diagram showing pulse waves obtainable by the electrical therapeutical apparatus in accordance with the invention.

In FIGS. 9 and 10, a multivibrator low frequency voltage oscillator 10 generates a voltage A of frequency in the cycle range of $T = \frac{1}{2}$-10 seconds equivalent to an intrinsic oscillation cycle of human body. The frequency may be conveniently modulated by a frequency converter.

The pulse A generated by the oscillator 10 is converted into a differentiation wave voltage B by means of a differentiation circuit 12. Subsequently, the voltage B is passed through a rectification circuit 14 to remove a negative component from the differentiation wave voltage B thereby to obtain a differentiation wave voltage C containing a positive component only.

The differentiation wave voltage C thus gained is applied to an input terminal of a pulse monostable multivibrator 16 to obtain a square wave voltage D having a saturation time "$t$" of less than 2 seconds which is in turn differentiated by a differentiation circuit 18 to obtain a differentiation wave voltage E of a single cycle pulse which oscillates in the positive and negative directions at 1/5,000 seconds.

The cycle of the differentiation wave voltage E conforms to a cycle at the frequency of the pulses generated by muscular motion potential created when an impulse from a center of the cerebrum is sent to the muscle so that an excellent stimulation is given to the human body. The differentiation wave voltage D is further passed through a power amplifier 20 for a convenient amplification and then supplied to a conductive needle 22 which is punctured into an affected point of the human body thereby to obtain anesthetic and analgesic effects.

The group pulses seen in FIGS. 5 - 7 can be obtained similarly, by the circuit shown in FIG. 15 wherein a converter for generating group pulses 10' provides an output directly to the input terminal of the differentiation circuit 18 to provide the pulse E.

Figure 11:
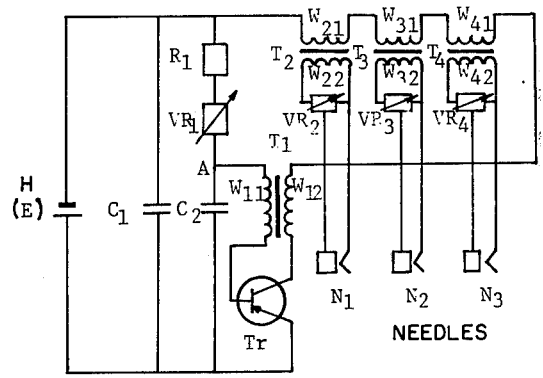
FIG. 11 is a circuit diagram of the electrical therapeutic apparatus of another embodiment according to the invention.

In the embodiment shown in FIG. 11, between a positive terminal and a negative terminal of a power source H are inserted a capacitor $C_1$ and a time constant circuit including a resistance $R_1$, a variable resistance $VR_1$ and a capacitor $C_2$.

A transistor $Tr$ of PNP type at its base is connected through a primary winding $W_{11}$ of a transformer $T_1$ to a middle point A between the variable resistance $VR_1$ and the capacitor $C_2$, at its emitter to a positive terminal of the power source H and a collector thereof is connected through a secondary winding $W_{12}$ combined in reversed polarity with the primary winding and the primary windings $W_{21}$, $W_{31}$ and $W_{41}$ of the transformers $T_2$, $T_3$ and $T_4$ to a negative terminal of the power source H so that when a potential at the mid point A of the time constant circuit reaches a predetermined value, the base current is thus applied to render the transistor $Tr$ conductive. Between the secondary windings $W_{22}$, $W_{32}$ and $W_{42}$ of the transformers $T_2$, $T_3$ and $T_4$ are connected to conductive needles $N_1$, $N_2$ and $N_3$ through the variable resistances $VR_2$, $VR_3$, and $VR_4$.

In operation, a predetermined voltage is applied by the power source H to charge the capacitor $C_1$ in the polarity as shown in FIG. 11 while the capacitor $C_2$ is also charged through resistor $R_1$ and variable resistor $VR_1$. When the potential at the point A of the time constant circuit reaches a predetermined value the base current flows through the base of the transistor $Tr$ to render the transistor $Tr$ conductive. When the base current passes through the primary winding $W_{11}$ of the transformer $T_1$, the current flows in a first direction from the secondary winding $W_{12}$ to the primary windings $W_{21}$, $W_{31}$, $W_{41}$ of the transformers $T_2$, $T_3$ and $T_4$ so that a relatively small negative pulse is developed in an instant between the secondary windings $W_{22}$, $W_{32}$, and $W_{42}$.

Figure 12:
FIG. 12 is a diagram of the pulse wave obtainable by the embodiment of FIG. 11.

When the transistor $Tr$ is rendered conductive a discharge path for capacitor $C_1$ will be established through the primary windings $W_{21}$, $W_{31}$ and $W_{41}$ of the transformers $T_2$, $T_3$ and $T_4$ and through transistor $Tr$ and will flow in a direction opposite to the first direction so that a large positive pulse is applied across the secondary windings $W_{22}$, $W_{32}$ and $W_{42}$. It will be appreciated by virtue of the described circuit of FIG. 11 a pulse of a asymmetrical wave having a positive component greater than the negative component as shown in FIG. 12 is applied to the needles $N_1$, $N_2$ and $N_3$. The discharge time of the capacitors $C_1$ and $C_2$ is selected so that discharge will be substantially complete by the time the transistor $Tr$ is rendered non-conductive. Capacitors $C_1$ and $C_2$ will again be charged when the transistor $Tr$ is rendered non-conductive.

The electrical therapeutic apparatus in accordance with my invention has been used for 15,500 times and in respect to 1,300 patients of from 3 to 91 ages without entailing any substantial ill effects. From my clinical experiments, the pain threshold changes show a curve as illustrated in FIG. 13 wherein the percentage of pain threshold change is plotted against time.

My experiments also have proved that the frequencies suitable to various meridians are as mentioned below but not limitative.

| | |
|---|---|
| Large Intestine Meridian | 160 KHZ |
| Triple Warmer Meridian | 80 KHz |
| Small Intestine Meridian | 40 KHz |
| Lung Meridian | 16 KHz |
| Circulation Meridian | 8 KHz |
| Heart Meridian | 4 KHz |
| Stomach Meridian | 20 KHz |
| Gall Bladder Meridian | 1 KHz |
| Bladder Meridian | .5 KHz |
| Spleen and Pancreas Meridian | 200 KHz |
| Liver Meridian | 100 KHz |
| Kidney Meridian | 50 KHz |

Figure 14:
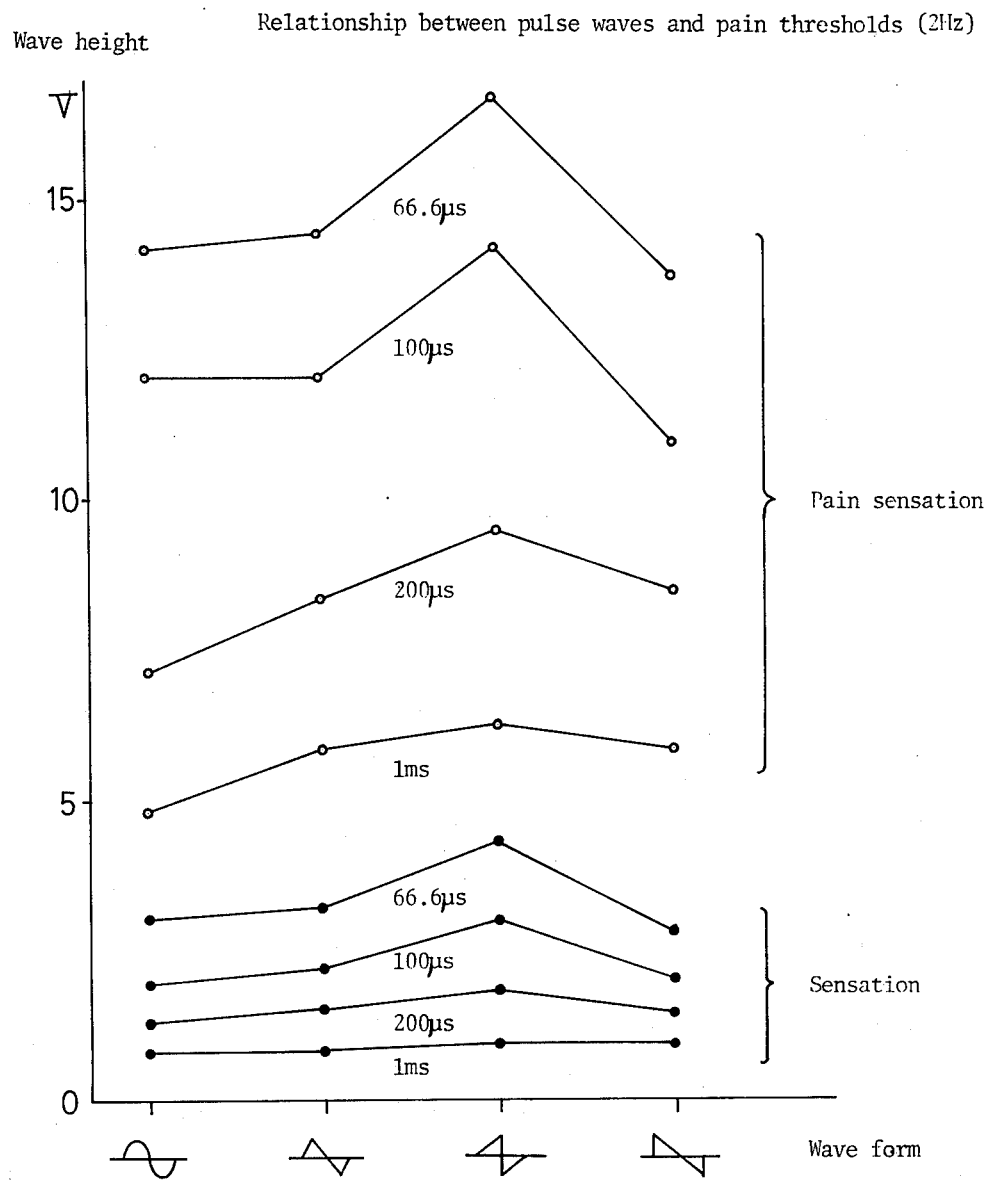
FIG. 14 is a graphical diagram showing the relationship between the pulse forms and the pain thresholds.

The pain threshold changes in accordance with the variation of the pulse waves are diagrammatically illustrated in FIG. 14 wherein wave height is plotted against given wave shapes, indicated symbolically.

While certain preferred embodiments of the invention have been illustrated by way of example in the drawings and particularly described, it will be understood that various modifications may be made in the apparatus and constructions and that the invention is no way limited to the embodiments shown.

I claim:

1. An electrical therapeutic apparatus which comprises a multi-frequency generating oscillator for generating voltages of predetermined shape over a frequency range including relatively low and relatively high frequencies, means for selecting a voltage of predetermined frequency and wave shape matched to an affected meridian, and conductive needle means for applying the selected voltage at puncture points on the human body at the affected meridian, said oscillator generating a series of voltage pulses at frequencies of between 2.5 KHz to 1.6 MHz at intervals of ½ to 10 seconds.

2. The apparatus according to claim 1, wherein each oscillation pulse has a positive and a negative impulse and has a duration of less than 1/5000 seconds, the difference between the positive component and the negative component of the pulse being substantially zero.

3. The apparatus according to claim 1 wherein said oscillator generates group of pulses, each pulse in the group having an oscillation cycle of less than 1/50 seconds, the group of pulses having a duration of 5 seconds, each pulse in the group being positively and negatively directed whereby the difference between the positive component and the negative component of each pulse is substantially zero.

4. The apparatus according to claim 3, wherein the voltage pulse is of asymmetric wave form.

5. The apparatus according to claim 1, wherein the frequency of the voltage pulses selected is related to the meridians as follows:

| MERIDIAN | FREQUENCY |
| --- | --- |
| Large Intestine Meridian | $16 \times 10^4$ Hz |
| Triple Warmer Meridian | $8 \times 10^4$ Hz |
| Small Intestine Meridian | $4 \times 10^4$ Hz |
| Lung Meridian | $16 \times 10^3$ Hz |
| Circulation Meridian | $8 \times 10^3$ Hz |
| Heart Meridian | $4 \times 10^3$ Hz |
| Stomach Meridian | $2 \times 10^4$ Hz |
| Gall Bladder Meridian | $1 \times 10^4$ Hz |
| Bladder Meridian | $0.5 \times 10^4$ Hz |
| Spleen & Pancrease Meridian | $2 \times 10^5$ Hz |
| Liver Meridian | $1 \times 10^5$ Hz |
| Kidney Meridian | $0.5 \times 10^5$ Hz |

* * * * *